(12) United States Patent
Gupta

(10) Patent No.: US 9,090,815 B2
(45) Date of Patent: Jul. 28, 2015

(54) METHOD OF USING ASPARAGINASE AS A POLYACRYLAMIDE ENZYME BREAKER

(75) Inventor: D. V. Satyanarayana Gupta, The Woodlands, TX (US)

(73) Assignee: Baker Hughes Incorporated, Houston, TX (US)

( * ) Notice: Subject to any disclaimer, the term of this patent is extended or adjusted under 35 U.S.C. 154(b) by 463 days.

(21) Appl. No.: 13/467,906

(22) Filed: May 9, 2012

(65) Prior Publication Data

US 2012/0285685 A1    Nov. 15, 2012

Related U.S. Application Data

(60) Provisional application No. 61/486,104, filed on May 13, 2011.

(51) Int. Cl.
| | |
|---|---|
| *E21B 43/22* | (2006.01) |
| *E21B 43/26* | (2006.01) |
| *C12N 9/82* | (2006.01) |
| *C09K 8/68* | (2006.01) |
| *B09C 1/00* | (2006.01) |
| *B09C 1/10* | (2006.01) |

(52) U.S. Cl.
CPC . *C09K 8/685* (2013.01); *C12N 9/82* (2013.01); *E21B 43/26* (2013.01); *B09C 1/002* (2013.01); *B09C 1/10* (2013.01); *C09K 2208/24* (2013.01)

(58) Field of Classification Search
CPC ............ C12N 9/00; C12N 9/82; B09C 1/002; B09C 1/10; C02F 3/34; C02F 5/08
See application file for complete search history.

(56) References Cited

U.S. PATENT DOCUMENTS

| | | | |
|---|---|---|---|
| 5,098,836 A | | 3/1992 | Stahl et al. |
| 5,165,477 A | * | 11/1992 | Shell et al. ................... 166/291 |
| 5,247,995 A | | 9/1993 | Tjon-Joe-Pin et al. |
| 5,604,186 A | * | 2/1997 | Hunt et al. .................... 507/204 |
| 5,678,632 A | * | 10/1997 | Moses et al. ................... 166/307 |
| 7,049,436 B2 | | 5/2006 | Gupta et al. |
| 7,385,019 B2 | | 6/2008 | Maroy et al. |
| 7,666,652 B2 | | 2/2010 | Matsui et al. |
| 8,372,786 B2 | * | 2/2013 | Berkland et al. ................ 507/90 |
| 2003/0092581 A1 | | 5/2003 | Crews |
| 2007/0141226 A1 | | 6/2007 | Elder et al. |
| 2008/0121395 A1 | | 5/2008 | Reddy et al. |
| 2008/0142230 A1 | | 6/2008 | Lau et al. |
| 2008/0283242 A1 | * | 11/2008 | Ekstrand et al. .............. 166/246 |
| 2010/0089580 A1 | | 4/2010 | Brannon et al. |
| 2010/0197530 A1 | | 8/2010 | Gupta et al. |
| 2010/0206569 A1 | | 8/2010 | Gupta et al. |
| 2011/0290491 A1 | | 12/2011 | Gupta et al. |
| 2012/0006549 A1 | | 1/2012 | Gupta et al. |
| 2012/0031618 A1 | | 2/2012 | Armstrong et al. |

FOREIGN PATENT DOCUMENTS

| | | |
|---|---|---|
| EP | 0583814 B1 | 10/1998 |
| WO | WO2004032648 A1 | 4/2004 |
| WO | WO2008128975 A1 | 10/2008 |

OTHER PUBLICATIONS

Acrylaway, www.acrylaway.novozymes.com.
Carman, P.S. and K.E. Cawiezel, "Successful Breaker Optimization for Polyacrylamide Friction Reducers Used in Slickwater Fracturing", SPE 106162, Jan. 29-31, 2007.

* cited by examiner

*Primary Examiner* — Zakiya W Bates
(74) *Attorney, Agent, or Firm* — John Wilson Jones; Jones & Smith, LLP

(57) ABSTRACT

Asparaginase, such as asparaginase derived from *Aspergillus oryzae*, may be used to break down or defragment polyacrylamides in oil field applications. The asparaginase is useful in reducing the viscosity of a fracturing fluid containing polyacrylamide and a crosslinking agent. The asparaginase is also useful in breaking down or defragmenting a polyacrylamide friction reducing agent, such as in a slickwater fracturing operation. Asparaginase may also be used to break down or defragment filter cakes containing polyacrylamide.

24 Claims, No Drawings

METHOD OF USING ASPARAGINASE AS A POLYACRYLAMIDE ENZYME BREAKER

This application claims the benefit of U.S. patent application Ser. No. 61/486,104, filed on May 13, 2011.

FIELD OF THE INVENTION

Asparaginases are used as enzyme breakers for polyacrylamides in oil field applications.

BACKGROUND OF THE INVENTION

Aqueous based well treatment fluids are commonly used in drilling, stimulation, completion and workover operations of subterranean formations. Treatment designs typically mandate such fluids to exhibit a certain level of viscosity. Polyacrylamides are often used in such fluids to provide the requisite viscosity. For instance, polyacrylamides are often used to form viscous gels to prevent fluid loss into the formation. In drilling fluids, such polymers serve to suspend solids and assist in floating debris out of the wellbore.

A common stimulation operation is hydraulic fracturing wherein fractures are created which extend from the wellbore into the formation. In this method, a viscous fracturing fluid containing proppant is introduced into the produced fracture under high pressure. The proppant remains in the produced fracture to prevent the complete closure of the fracture and to form a conductive channel extending from the wellbore into the treated formation and to provide a highly conductive pathway for hydrocarbons and/or other formation fluids to flow into the wellbore. In addition to increasing the capability of proppant transport into the fracture during the fracturing operation, viscosifying polymers also reduce friction, control fluid loss and control fracture geometry.

Filtrate from the fracturing fluid ultimately "leaks off" into the surrounding formation leaving a filter cake comprised of fluid additives. Such additives, including the viscosifying polymers used to provide fluid viscosity, are typically too large to penetrate the permeable matrix of the formation. Recovery of the fracturing fluid is therefore an important aspect to the success of the fracturing treatment.

Recovery of the fracturing fluid is normally accomplished by reducing the viscosity of the fracturing fluid (breaking) such that the fracturing fluid flows naturally from the formation. Thus, in addition to facilitating settling of the proppant in the fracture, the breaker also facilitates fluid flowback to the well.

Breakers work by reducing the molecular weight of the viscosifying agent. Common breakers for use in fracturing fluids include chemical oxidizers, such as hydrogen peroxide and persulfates. Chemical oxidizers produce a radical which then degrades the viscosifying agent. This reaction is limited by the fact that oxidizers work in a stoichiometric fashion. In addition, at low temperatures, such as below 120° F., chemical oxidizers are generally too slow to be effective and other catalysts are needed to speed the rate of reaction. At higher temperatures, chemical oxidizers react rapidly and, when they are encapsulated, are released prematurely, potentially leading to catastrophic loss of proppant transport. Since the use of chemical breakers in fracturing fluids at elevated temperatures typically compromise proppant transport and desired fracture conductivity, alternative sources for breakers have been sought.

Recently, interest has focused on slickwater fracturing in the stimulation of low permeability or tight gas reservoirs. In slickwater fracturing, a well is stimulated by pumping water at high rates into the wellbore, thereby creating a fracture in the productive formation. Slickwater fluids are basically fresh water or brine having sufficient friction reducing agent(s) to minimize tubular friction pressures. Slickwater fracturing fluids usually have viscosities only slightly higher than unadulterated fresh water or brine. The characteristic low viscosity of such fluids facilitates reduced fracture height growth in the reservoir during stimulation.

When aqueous fluids (like slickwater fracturing fluids) not containing a viscosifying polymer are used in stimulation, the pressure during the pumping stage is normally lower than that required in fracturing treatments using viscosifying polymers. The frictional drag of the frac fluid is lowered by the presence of the friction reduction agent(s) in the slickwater fluid. Polyacrylamides are often used as friction reducing agents in slickwater fracturing.

While slickwater fluids introduce less damage into the formation in light of the absence of viscosifying polymers, the friction reduction agent, if left in the formation, can cause formation damage. Effective means of degrading friction reduction agents in slickwater fracturing fluids is desired in order to minimize damage to the treated formation.

Lately, "hybrid" fracturing techniques have evolved wherein a conventional gelled and/or crosslinked fracturing fluid is used as a pad fluid which precedes the introduction of a proppant laden slickwater slurry. The relatively high viscosity gelled fluid provides increased fracture width and improved fluid efficiency, thereby mitigating the limitations of slickwater. Unfortunately, however, viscosifying polymers (such as polyacrylamides) used in such viscosified fluids form filter cakes on fracture faces which cause conductivity damage. Since the concentration of proppant in fracturing fluids free of viscosifying polymer is low and results in propped fracture widths typically no greater than one layer of proppant (±0.5 mm), any effective fracture width lost to the deposition of a filter cake often has catastrophic consequences on fracture conductivity.

Polyacrylamides, when used in oilfield applications have been proven difficult to break or degrade with conventional chemical oxidizers. Alternatives have therefore been sought for degrading polyacrylamides used in oilfield applications.

SUMMARY OF THE INVENTION

A hydrocarbon-bearing subterranean formation or a well penetrated by a subterranean formation may be treated with an aqueous well treatment fluid containing an asparaginase. The asparaginase may act as a breaker, for instance, in the hydrolysis of a polyacrylamide.

In an embodiment, asparaginase may be used in a hydraulic fracturing operation to break down or defragment polyacrylamide and thus decrease the viscosity of a fracturing fluid containing polyacrylamide as viscosifying agent.

In another embodiment, asparaginase may be used as a breaker to break down or defragment a polyacrylamide friction reducer.

In a particular embodiment, asparaginase is used in slickwater fracturing to break down a polyacrylamide friction reducer.

In another embodiment, asparaginase is used in a drilling, completion or workover operation to break down or defragment a viscous fluid containing polyacrylamide.

In a particular embodiment, asparaginase is used to decompose or break down a polyacrylamide containing filter cake, the filter cake being formed, for instance, during drilling or completion of a well.

DETAILED DESCRIPTION OF THE PREFERRED EMBODIMENTS

Any number of asparaginases may be used as the enzyme to break down polyacrylamide during a well treating operation. The well treating operation may include drilling, stimulation, completion and workover operations of oil, gas and geothermal wells and subterranean formations penetrated by such wells.

Suitable asparaginases include those which are thermostable at temperatures encountered during well treatment operations, typically between from about 20 to about 120° C. Asparaginases are believed to hydrolyze the amide linkages of the polyacrylamide and thus defragment or decompose the polyacrylamide in-situ.

Preferred are asparaginases derived from *Aspergillus niger; Aspergillus oryzae, Penicillium citrinum, Aspergillus fumigatus* and *Aspergillus nidulans*. For instance, preferred asparaginases include those disclosed in WO2004/030468 encompassing an amino acid sequence of asparaginase derived from *Aspergillus niger*; WO2004/032648 encompassing a sequence derived from *Aspergillus oryzae* and *Penicillium citrinum*; and WO2004/032648 encompassing a sequence from *Aspergillus fumigatus* and *Aspergillus nidulans*, all of which are herein incorporated by reference. A further example of an asparaginase is that, disclosed in the literature, having an amino acid sequence and crystal structure of L-asparaginase from *Erwinia chrysanthemi*. Further preferred are asparaginases disclosed in U.S. Pat. No. 7,666,652, herein incorporated by reference and especially those asparaginases from *Aspergillus oryzae*, including those based on a homologous enzyme from *Erwinia chrysanthemi*.

The asparaginase breaks down or defragments the polyacrylamide. Exemplary polyacrylamides include homopolymers and copolymers of acrylamide, (meth)acrylamide, and acrylamide and (meth)acrylamide derivatives including water soluble polyacrylamides and copolymers thereof (such as copolymers of acrylamide with acrylate monomers).

In an aspect, the acrylamide can be any amide of an ethylenically unsaturated carboxylic acid. For instance, the polyacrylamide may be a homopolymer or copolymer of a monomer of formula:

$$R^1CONR^2R^3 \qquad (I)$$

wherein $R^1$ is a linear or branched group chosen from alkyl or alkenyl groups, including those containing from one to 12 carbon atoms, and $R^2$ and $R^3$ can be hydrogen or linear or branched groups chosen from alkyl or alkenyl groups, where at least one of $R^1$, $R^2$ and $R^3$ is an alkenyl. Examples of suitable amides include acrylamide; N-substituted hydrosoluble derivatives of acrylamide, such as N,N-dimethylacrylamide; and hydrosoluble N-vinylamides, such as N-vinylacetamide.

Acrylamide of formula (I) may further be polymerized with anionic monomers, cationic and non-ionic monomers. Examples of suitable anionic monomers include acrylic acid, salts of acrylic acid thereof, methacrylic acid, salts of methacrylic acid, maleic anhydride, acrylamido-methylpropyl sulfonic acid, salts of acrylamido-methylpropyl sulfonic acid, styrenesulfonic acid, salts of styrenesulfonic acid, vinylsulfonic acid, and salts of vinylsulfonic acid. Examples of suitable cationic monomers include quaternised or non-quaternised vinylpyridine and vinyl phosphonate. Other examples of suitable non-ionic and ionic monomers are disclosed in U.S. Pat. No. 7,385,019, herein incorporated by reference. Exemplary non-ionic monomers include acrylamido-methylpropyl sulfonic acid (AMPS).

Preferred species of polyacrylamides may include aminomethylated polyacrylamides and poly(meth)acrylamides (such as di-methylaminopropyl methacrylamide and di-methylaminopropyl acrylamide), polymers of ammonium or alkali metal salts of acrylamido-methyl propane sulfonic acid (AMPS) including 2-acrylamido-2-methylpropane sulfonates, acrylamido-methyl propane sulfonic acid and salts/acrylic acid copolymers (AMPS/AA), phosphinated maleic copolymers (PHOS/MA), salts of polymaleic acid/acrylic acid/acrylamido-methyl propane sulfonate terpolymers (PMA/AMPS) and copolymers of acrylamide, acrylamidomethylpropanesulfonic acid, and vinyl phosphonate.

In an aspect, the homo or co-polymer of acrylamide may have a K-value of greater than about 375.

The asparaginase may be present in a fracturing fluid containing the polyacrylamide as viscosifying agent. When used in fracturing fluids, a crosslinking agent is normally used also to further increase viscosity. Any crosslinking agent capable of hydrogen bonding with the viscosifying polymer may be employed. Suitable crosslinking agents include a borate ion releasing compound, an organometallic or organic complexed metal ion comprising at least one transition metal or alkaline earth metal ion as well as mixtures thereof.

When used in a fracturing fluid, any proppant known in the art may be used in the well treatment fluid. Suitable proppants include quartz sand grains, glass and ceramic beads, walnut shell fragments, aluminum pellets and nylon pellets. Other suitable proppants include ultra lightweight proppants having an apparent specific gravity less than or equal to 2.45, preferably less than or equal to 1.75, most preferably less than or equal to 1.25. Suitable ULW particulates include those set forth in U.S. Patent Publication No. 20050028979, published on Feb. 10, 2005, herein incorporated by reference.

The optimum pH of a fracturing fluid containing polyacrylamide as viscosifying polymer typically is between from about 6.0 to about 11.0. In some instances, it is desirable for the fluid to have a pH regulating substance to ensure the requisite pH.

The asparaginase has particularly applicability in the stimulation of low permeability gas reservoirs especially those having a permeability less than 1 millidarcy. Slickwater fracturing is often employed in the fracturing of such tight formations and is particularly desirous when stimulating shale formations and tight gas sands, as well as limestone.

In slickwater fracturing, polyacrylamides are typically used to reduce the frictional drag of the aqueous fluid against tubulars within the wellbore. In slickwater fracturing, a crosslinking agent is typically not present in the fluid. When polyacrylamides are used in well treatment fluids as a polymeric friction reducer, the asparaginase reduces the molecular weight of the friction reducing agent. The defragmented components of the friction reducing agent may then be removed from the wellbore and formation damage from the friction reducing agent is thereby minimized. The amount of friction reducing agents in such well treatment fluids is generally from about 0.25 to about 5 gallons of a 40% active polyacrylamide emulsion per thousand gallons of water. Further, use of the well treatment agent in slickwater fracturing improves leakoff control of filtrate into the formation.

In addition to functioning as a stimulation fluid, the aqueous well treatment fluids described herein may also be used as a well treatment fluid to clean up a fluid loss pill typically used during completion operations. In this case, the well treatment fluid aids in the removal of the filter cake formed by the fluid loss pill. The filter cake, in some instance, may become embedded in the formation. The asparaginase is used to break down the polyacrylamide in the filter cake. The well treatment fluid therefore assists in the removal of the filter cake defragmenting the polymeric component present in the filter cake.

Similarly, the aqueous well treatment fluids described herein may also be used as a well treatment fluid to remove the filter cake from drilling fluid or drill-in fluid formed during drilling operations. In this case, the well treatment fluid aids in the removal of the filter cake formed by the drilling fluid or drill-in fluid being deposited directly against the formation. The filter cake, in some instance, may become embedded in the formation. Removal of the filter cake is effectuated by breaking down the polymeric component of the filter cake in the manner described above.

In some instances, the asparaginase, especially when present in a proppant laden fluid, may enhance degradation of the filter cake during flow-back of the proppant laden fluid. As such, the asparaginase increases fracture conductivity within the formation.

While the method described herein may normally be used in horizontal wells, the method may be used in vertical wells.

In some instances, it is desirable to use a pH buffer to maintain the fluid containing the asparaginase in a pH range of about 4.5 to about 5.25. For example, the pH buffer may contain acetic acid and sodium acetate. In another example, the pH buffer may contain acetic acid, sodium acetate, formic acid, or a combination thereof.

Since the asparaginase is thermostable, it may be used in a fluid introduced into a wellbore exposed to high downhole temperatures without degradation.

Typically, the asparaginase is introduced into the wellbore as an aqueous enzyme solution. The weight percentage of enzyme solution in the fluid is dependent upon the number of units of enzyme activity in the aqueous enzyme solution. For instance, the amount of an aqueous enzyme solution having 30,000 units of enzyme activity in the treatment fluid is generally between from about 0.05 to about 1.3 weight percent, preferably from about 0.103 to about 0.206 weight percent. The weight percentage of an enzyme solution containing a different unit of enzyme activity may be determined using the designated weight percentage for the enzyme solution containing 30,000 units of enzyme activity.

The asparaginase may be added to the well or subterranean formation in the same fluid as the polyacrylamide. Alternatively, the asparaginase may be added to the well or subterranean formation before or after the addition of the polyacrylamide. For instance, when used in hydraulic fracturing, the asparaginase is typically added in a fluid with the polyacrylamide or is added subsequent to the addition of the fluid containing the polyacrylamide. When used to defragment or destroy a filter cake, the asparaginase is typically added to the well or formation after the addition of the polyacrylamide.

Any amount or concentration of asparaginase suitable for degrading or reducing the viscosity of polyacrylamide in a fluid or to cause degradation of a filter cake containing embedded polyacrylamide which is formed at the fracture face of the formation may be used. Typically, such breakers are included in their respective fluid in a concentration of between about 0.1 lb/1000 gals. and about 10 lb/100 gals.

The foregoing disclosure and description of the invention is illustrative and explanatory thereof, and various changes in the details set forth above may be made without departing from the spirit of the invention.

What is claimed is:

1. A method of treating a well or a subterranean formation penetrated by a well wherein the well has been treated with a fluid containing a polyacrylamide, the method comprising introducing into the well or subterranean formation a fluid comprising an aqueous solution of an asparaginase breaker wherein the amount of asparaginase breaker in the fluid is between from about 0.1 lb/1,000 gals to about 10 lb/100 gals and degrading the polyacrylamide with the asparaginase.

2. The method of claim 1, wherein the asparaginase is used to remove a filter cake by breaking down polyacrylamide in the filter cake.

3. The method of claim 2, wherein the asparaginase is used to remove a filter cake formed from a drilling fluid or a drill-in fluid being introduced into the well.

4. The method of claim 1, wherein the asparaginase is derived from *Aspergillus oryzae*.

5. The method of claim 1, wherein the polyacrylamide is a homopolymer or copolymer derived from a monomer of formula:

$$R^1 CONR^2 R^3 \quad (I)$$

wherein $R^1$ is a linear or branched alkyl or alkenyl group, and $R^2$ and $R^3$ are independently selected from hydrogen or a linear or branched alkyl or alkenyl group.

6. The method of claim 5, the polyacrylamide is a homopolymer or copolymer derived from acrylamide; N-substituted hydrosoluble derivatives of acrylamide; and hydrosoluble N-vinylamides.

7. The method of claim 5, wherein the polyacrylamide is a copolymer further derived from a monomer selected from the group consisting of acrylic acid, salts of acrylic acid, methacrylic acid, salts of methacrylic acid, maleic anhydride, acrylamido-methylpropyl sulfonic acid, salts of acrylamido-methylpropyl sulfonic acid, styrenesulfonic acid, salts of styrenesulfonic acid, vinylsulfonic acid, salts of vinylsulfonic acid, quaternised and non-quaternised vinylpyridine and vinyl phosphonate, and acrylamido-methylpropyl sulfonic acid.

8. The method of claim 1, wherein the asparaginase is introduced into the well or subterranean formation during a hydraulic fracturing operation.

9. The method of claim 1, wherein the asparaginase is introduced into a well or subterranean formation during a slickwater fracturing operation.

10. The method of claim 1, wherein the polyacrylamide is a viscosifying agent and further wherein the fluid contains a crosslinking agent.

11. The method of claim 1, wherein the asparaginase is used to remove a filter cake formed by a fluid loss pill.

12. The method of claim 1, wherein the asparaginase is added to the well or subterranean formation in the fluid containing the polyacrylamide.

13. The method of claim 1, wherein the asparaginase is added to the well or subterranean formation before or after the addition of the fluid containing the polyacrylamide.

14. The method of claim 1, wherein the pH of the fluid is between about 4.5 to about 5.25.

15. A method of treating a subterranean formation which comprises:
   (a) introducing into the wellbore a fluid containing a polyacrylamide and a crosslinking agent and further introducing into the wellbore an asparaginase in an aqueous solution; and
   (b) breaking the viscosity of the fluid by defragmenting the polyacrylamide with the asparaginase.

16. The method of claim 15, wherein the asparaginase is added to the wellbore in the same fluid containing the polyacrylamide wherein the amount of asparaginase in the fluid is between from about 0.1 lb/1,000 gals to about 10 lb/100 gals.

17. The method of claim 15, wherein the asparaginase is added to the wellbore before or after the addition of the fluid containing the polyacrylamide.

18. The method of claim 15, wherein the asparaginase is derived from *Aspergillus oryzae*.

19. In a method of treating a well or a subterranean formation penetrated by a well with a fluid containing a polyacrylamide and then degrading the polyacrylamide with a breaker, the improvement comprising introducing into the well or subterranean formation an aqueous solution of a breaker comprising *Aspergillus oryzae*.

20. A method of removing a polyacrylamide containing filter cake in a well wherein the filter cake is formed during drilling or completion of the well, the method comprising pumping into the well a fluid comprising asparaginase and defragmenting the polyacrylamide with the asparaginase.

21. A method of slickwater fracturing a subterranean formation having a permeability less than 1 millidarcy comprising:
   (a) introducing into the wellbore penetrating the subterranean formation an aqueous solution of an asparaginase and an aqueous well treatment fluid void of a viscosifying polymer, wherein the well treatment fluid comprises a polyacrylamide friction reducing agent; and
   (b) reducing the viscosity of the well treatment fluid by defragmenting the polyacrylamide friction reducing agent with the asparaginase.

22. The method of claim 21, wherein the asparaginase is added to the wellbore in the same fluid containing the polyacrylamide.

23. The method of claim 21, wherein the asparaginase is added to the wellbore before or after the addition of the fluid containing the polyacrylamide.

24. The method of claim 21, wherein the asparaginase is derived from *Aspergillus oryzae*.

\* \* \* \* \*